United States Patent
Yang et al.

(12) 
(10) Patent No.: US 6,256,525 B1
(45) Date of Patent: Jul. 3, 2001

(54) CATHETER DISTAL END ASSEMBLIES WITH BONDED SURFACE COATINGS

(75) Inventors: Yi Yang, San Francisco; Josef Koblish, Sunnyvale; Russell B. Thompson, Los Altos; David K. Swanson, Mountain View, all of CA (US)

(73) Assignee: EP Technologies, Inc., San Jose, CA (US)

( * ) Notice: Subject to any disclaimer, the term of this patent is extended or adjusted under 35 U.S.C. 154(b) by 0 days.

(21) Appl. No.: 09/573,447

(22) Filed: May 16, 2000

Related U.S. Application Data

(63) Continuation of application No. 09/032,707, filed on Feb. 27, 1998, now Pat. No. 6,097,976.

(51) Int. Cl.⁷ ...................................................... A61E 5/04
(52) U.S. Cl. .............................. 600/373; 600/374; 606/41
(58) Field of Search ........................ 606/32, 34, 35–41, 606/45–50; 600/373, 374, 380, 381, 395; 427/2.1, 2.12, 58; 604/264–266, 523, 524; 607/122–124

(56) References Cited

U.S. PATENT DOCUMENTS

| | | |
|---|---|---|
| 3,568,660 | 3/1971 | Crites et al. .............................. 128/2 |
| 3,635,212 | 1/1972 | Watanabe et al. . | 
| 3,910,008 | 10/1975 | Johnson ............................. 53/112 A |
| 4,402,319 | 9/1983 | Handa et al. . |
| 5,304,120 | 4/1994 | Crandell et al. ......................... 604/52 |
| 5,507,744 | 4/1996 | Tay et al. ................................ 606/41 |
| 5,508,899 | 4/1996 | Fan et al. ................................. 604/96 |
| 5,531,715 | 7/1996 | Engelson et al. ..................... 604/265 |
| 5,804,318 | 9/1998 | Pinchuk et al. . |
| 5,954,702 | 9/1999 | Lai et al. .............................. 604/283 |
| 5,991,650 | * 11/1999 | Swanson et al. ..................... 600/374 |

FOREIGN PATENT DOCUMENTS

WO97/45156    4/1997    (WO) .

* cited by examiner

*Primary Examiner*—Linda C. M. Dvorak
*Assistant Examiner*—David M. Ruddy
(74) *Attorney, Agent, or Firm*—Lyon & Lyon LLP

(57) ABSTRACT

Invasive medical catheters with distal end assemblies having a protective surface coating bonded thereto are constructed by applying a hydrophilic primer to at least a portion of a tubular polymer body. The primer coating chemically bonds to the polymer substrate by developing covalent bonding or cross linking with the substrate. A plurality of printed electrode elements are then formed on the polymer body, e.g., by a pad printing process. Once the primer coating is bonded to the polymer body, the assembly is coated with a regenerated cellulose layer, e.g., by a viscose process well known in the art. The primer coating, already bonded to the catheter body, is then bonded with the regenerated cellulose at an elevated temperature. After curing, the polymer body, primer coating and regenerated cellulose layer become a single composite material, thereby preventing the regenerated cellulose coating from any movement relative to the polymer body, and providing a secure protective layer over the electrodes.

14 Claims, 4 Drawing Sheets

CATHETER DISTAL END ASSEMBLIES WITH BONDED SURFACE COATINGS

This application is a continuation of Ser. No. 09/032,707 Feb. 27, 1998 U.S. Pat. No. 6,097,976.

FIELD OF THE INVENTION

The present invention relates generally to invasive diagnostic and therapeutic medical catheter assemblies and, more particularly, to distal end surface coatings used on such assemblies.

BACKGROUND

Conventionally, external components located on invasive medical catheters, such as an electrode or thermocouple, are manually placed on the catheter body—e.g., in the form of wound coil or a conductive band. The components are typically held in position with an adhesive, a process which is relatively time consuming and expensive.

One notable problem with this construction is that if an external component is not properly fit onto the catheter body, small openings and crevices at the edges of the component may be formed, allowing for the ingress and retention of bodily fluids or tissue during use. Additionally, this traditional catheter-electrode construction can result in undesirably high electrode edge effects caused by the sharp transition between the conductive electrode band and the immediately adjacent non-conductive catheter body.

Further, because the electrode components come into direct contact with a patient's blood stream and body tissues during use, non-biocompatible (i.e., toxic) materials otherwise having advantageous characteristics for use in an externally mounted electrode, including silver or lead, cannot be used.

Therefore, a need has existed for an improved external electrode constructions for invasive medical catheters.

Such improvements are disclosed and described in U.S. Pat. No. 5,991,650, which is fully incorporated herein by reference for all it discloses and describes. As disclosed therein, a metal-based conductive ink is used to form exterior electrodes on a non-conductive polymer catheter tubing by processes such as pad printing, vapor deposition, ion beam assisted deposition, electroplating or other printed circuit manufacturing processes. Preferred ink materials include a silver/silver chloride filled polyurethane composite ink that is flexible and highly electrically conductive after the polyurethane is cured. The printed ink electrodes are then covered with an electrically conductive outer coating, preferably formed from a material comprising regenerated cellulose.

The regenerated cellulose coating secures the underlying electrode structures onto the catheter, while still enabling electrical contact between the electrodes and surrounding body tissue structures. One advantage of using regenerated cellulose for the protective coating is that regenerated cellulose is ion-permeable, thereby allowing ionic transfer of electrical energy from the electrodes into the patient's bloodstream and/or body tissue, while preventing macromolecules, such as blood proteins, from contacting the printed electrode material during use.

Additionally, because the regenerated cellulose surface coating produces a smooth outer surface to the distal end assembly, lead wires and temperature sensing devices can be bonded to the exterior surface of electrodes and then coated to produce a smooth outer surface, thus providing a simple, inexpensive manufacturing method for the attachment of such components to the electrodes.

In particular, the regenerated cellulose coating acts as a mechanical barrier between the catheter components, such as electrodes, preventing ingress of blood cells, infectious agents, such as viruses and bacteria, and large biological molecules such as proteins, while providing electrical contact to the human body. As a result the electrodes can be made using more efficient processes (such as pad printing) that have been previously rejected due to lack of robustness when directly exposed to bodily tissues on a catheter surface.

The regenerated cellulose coating also acts as a biocompatible barrier between the catheter components and the human body, whereby the components can now be made from materials that are somewhat toxic (such as silver or copper), because the diffusional distance to tissues is increased substantially, and because a lower percentage of the metallic surface is exposed (both directly and indirectly) to the tissue.

In addition, coating electrodes with regenerated cellulose decreases the effect of convective cooling on the electrode during RF energy delivery. That is, since regenerated cellulose is a poor thermal conductor when compared to metal, the effect of convective cooling by blood flowing past the regenerated cellulose coated electrodes is diminished. This provides better control for the lesion-generating process because the hottest tissue temperature is closer to the ablation electrode.

Furthermore, the regenerated cellulose coating decreases the edge effects attributed to delivering RF energy to the electrode having sharp transition between the conductive electrode and insulating catheter tubing. The current density along the electrode and power density within tissue are more uniform, which reduces the incidence and severity of char and/or coagulum formation. The more uniform current density along the axis of the catheter also results in a more uniform temperature distribution at the electrode, which decreases the requirement for precise placements of the temperature sensors at the ablation electrodes.

Notably, intimate contact between the regenerated cellulose coating and the conductive electrodes on the catheter body is required to ensure reliable pacing, electrogram sensing, or ablation through the microporous structure of the regenerated cellulose coating. While the regenerated cellulose coating closely conforms to the catheter body, e.g., like a skin, it does not actually adhere to the polymers commonly used to make catheters, such as, e.g. polyether block amides (PEBAs). Nor does it adhere to metal-based printed ink materials. Instead, a mechanical fit of the regenerated cellulose "jacket" on the distal end of the catheter is relied upon.

Thus, if the distal end of the catheter is aggressively torqued or twisted, the regenerated cellulose jacket can at times "barber pole" or become axially wrinkled or blistered, resulting in a loss of direct contact of the coating and the underlying electrode structure. This can result in poor, intermittent, or even loss of electrical contact with the electrode. This compromised electrode contact can result in noisy recordings, inconsistent pacing thresholds, and unpredictable (and therefore uncontrollable) ablation conditions, depending upon the particular application.

Further, if the catheter is introduced through a close-fitting introducer (e.g., such as a pre-shaped guide sheath), the regenerated cellulose coating can become stretched axially relative to the underlying catheter body structure.

Because there is no conductive fluid such as saline between the electrode and regenerated cellulose coating, the electrical path can become intermittent or open where the two materials become separated.

Thus, for reasons of durability, consistent signal quality, pacing capabilities and ablation, it would be beneficial to improve upon the disclosure of U.S. patent application Ser. No. 08/879,343, and provide a coherent composite assembly for protecting the distal portion of the finished catheter device.

SUMMARY OF THE INVENTION

The present invention provides invasive medical catheters with distal end assemblies having a protective surface coating bonded thereto.

In an exemplary preferred embodiment, a base primer is applied over a non-conductive thermoplastic elastomer polymer body. The primer chemically bonds to the polymer body substrate by developing covalent bonding or cross linking with the substrate. A plurality of printed electrode elements are then formed on the polymer body, e.g., by a pad printing process. Once the primer coating is bonded to the polymer body, the entire assembly is coated with a solubilized cellulose derivative solution. The solubilized cellulose derivative is then converted back into a pure cellulose structure by a regeneration process, such as viscose process which is well known in the art.

The primer, already bonded to the polymer body, is then bonded to the regenerated cellulose by heat treating at an elevated temperature. After curing, the polymer body, primer coating and regenerated cellulose layer become a single composite material, thereby preventing the regenerated cellulose coating from any movement relative to the polymer body.

In alternate preferred embodiments, the primer may be applied over the top of the printed electrodes. In this case, a selected primer will preferably have a significantly lower electrical resistivity, so as to not interfere with the electrical conductivity of the electrodes.

In further alternate preferred embodiments, a standard adhesive, such as cyanoacrylate or epoxy, may be used in lieu of the base primer. Also, the primer or adhesive coating may be applied only to selected portions of the polymer body, e.g., on the non-conductive areas between electrodes, or only at end points of the distal end assembly.

Other objects and features of the present invention will become apparent from consideration of the following detailed description of preferred embodiments, taken in conjunction with the accompanying drawings.

BRIEF DESCRIPTION OF THE DRAWINGS

The drawings illustrate both the design and utility of the present invention, in which similar elements in different embodiments are referred to by the same reference numbers for purposes of ease in illustration, wherein.

DETAILED DESCRIPTION OF THE PREFERRED EMBODIMENTS

Figure 1:
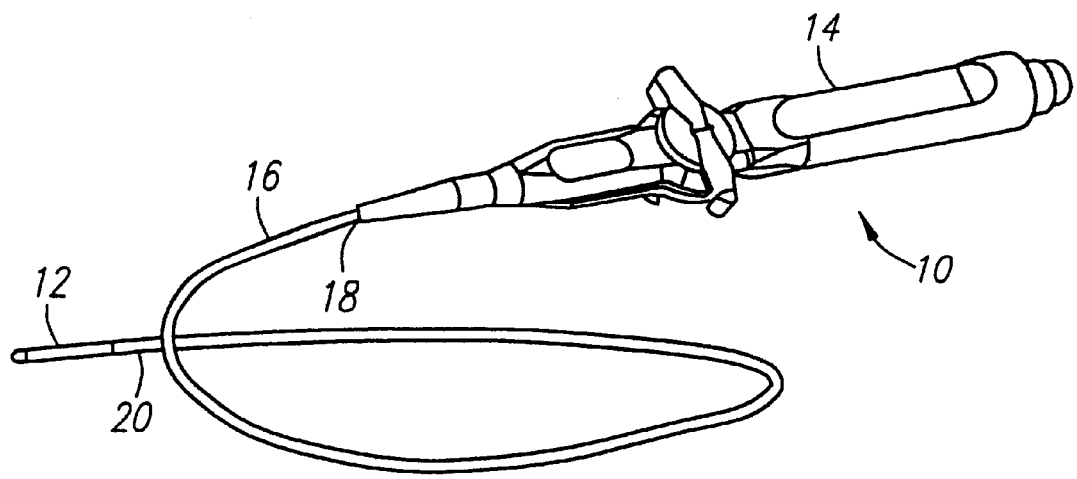
FIG. 1 is a perspective view of a catheter device provided with a distal end external electrode assembly.
Figure 2:
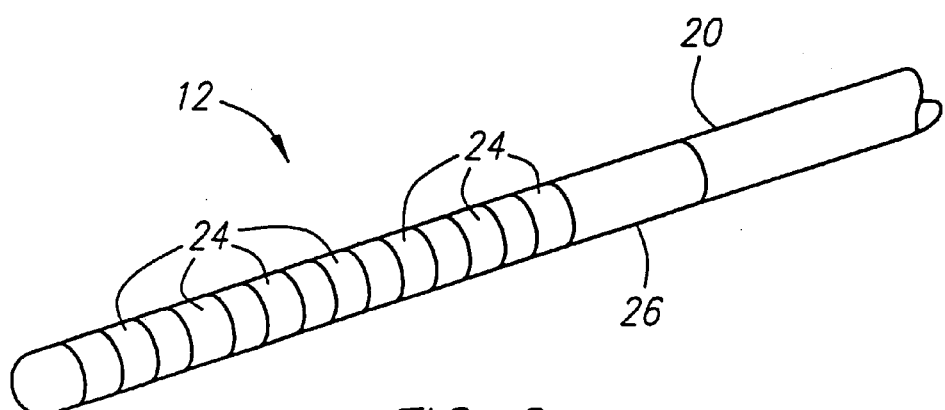
FIG. 2 is a perspective view of the distal end assembly of the catheter device of FIG. 1.

Referring to FIGS. 1–2, an exemplary catheter device 10 generally includes a handle 14 and an elongate tubular catheter body 16. The catheter body 16 has a proximal end 18 engaging the handle 14 and a distal end 20 engaging a distal end assembly 12. The distal end assembly 12 includes a non-conductive tubing 26 having a plurality of external conductive electrodes 24 formed thereon.

By way of example, the catheter device 10 may be a therapeutic instrument for use in an ablation procedure, wherein the distal end electrodes 24 would be configured for creating lesion patterns in internal body tissue. By way of alternate example, the catheter device 10 may be a diagnostic instrument for use in detecting the location of aberrant electrical pathways in a patient's myocardial tissue, wherein the distal end electrodes 24 would be configured for detecting electrical activity in body tissue.

The distal end tubing 26 of the distal end assembly 12 is preferably formed from a non-conductive thermoplastic elastomer, such as polyether block amides (PEBA), and may be extruded to provide a substantially smooth outer surface as shown. Alternatively, the outer surface of the distal body portion 26 may include a longitudinal channel, skive and the like (not shown) to facilitate assembly of the electrodes thereon.

In alternate preferred embodiments, the distal end assembly 12 can be formed on the distal end portion 18 of the elongate catheter body 16—i.e., wherein the distal end tubing 26 is part of the distal elongate catheter 16.

For purposes of illustration, the distal end assembly 12 of FIGS. 1–2 is a "generic" embodiment of the more specific preferred distal end assemblies disclosed and described in FIGS. 3–7.

Figure 3:
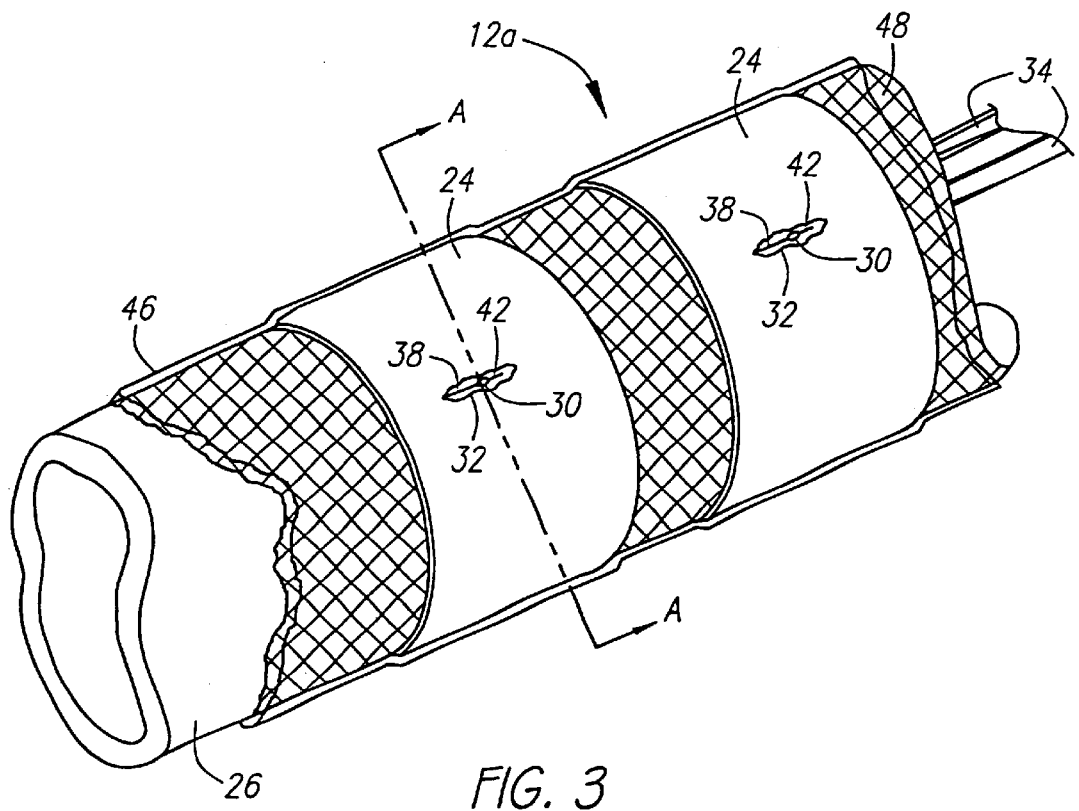
FIG. 3 is an enlarged, partially cut-away view of a first preferred distal end assembly for the catheter device of FIG. 1.

Referring to FIG. 3, in a first preferred distal end assembly 12a, a primer coating 48 is applied over the surface of the distal end tubing 26 prior to formation of the electrodes 24. By way of example, the primer coating 48 may be applied over the distal end assembly 12a by dipping or spraying the distal end tubing 26 in or with a commercially available base primer, until a finished thickness of no more than about 0.0005 inch is obtained.

The selected primer may contain from about 85% wt to 95% wt, and preferably about 91% wt to 93% wt polyester-polyurethane aqueous dispersion such as Bayhydrol PR240™, and 5% wt to 15% wt, and preferably about 4% wt to 6% wt polyfunctional aziridine crosslinker such as Crosslinker CX-100™. Because it underlies the electrodes 24, the selected primer coating 48 should preferably have a relatively high electrical resistivity—e.g., more than about $10^5$ ohm-cm at a range of 0.1 to 500 kHz.

The primer coating 48 is then cured, for example, by heating the coated distal end assembly 12a (e.g., between 35° C. to 65° C. for 1 to 2 hours), or exposing it to high intensity ultraviolet light, causing it to bond to the distal end tubing 26. In particular, the primer coating 48 bonds to the distal end tubing 26 by developing a covalent bond or cross linking with the thermoplastic elastomer.

After the primer 48 is cured, the electrodes 24 are formed at predetermined locations on the primer-coated distal end assembly 12a. The electrodes 24 are preferably longitudinally spaced along the distal end tubing 26, such that non-conductive areas of the distal end tubing 26 remain between consecutive electrodes.

The electrodes 24 may be formed using a variety of methods, such as those described in the above-incorporated U.S. Pat. No. 5,991,650. In one preferred embodiment, the electrodes 24 are formed from a conductive ink compound, such as a silver-based conductive polyurethane ink, which is pad printed onto the distal end tubing 26. Alternatively, to increase their radiopacity, the electrodes 24 may be formed by multiple layers of different ink compounds (not shown). For example, the electrodes 24 may have a tungsten-filled polyurethane ink bottom layer for radiopacity and a silver-filled polyurethane ink top layer for electrical conductivity. Other metal-based conductive ink compounds, such as platinum-based or copper-based epoxies may also be used to form the electrodes 24.

Figure 4:
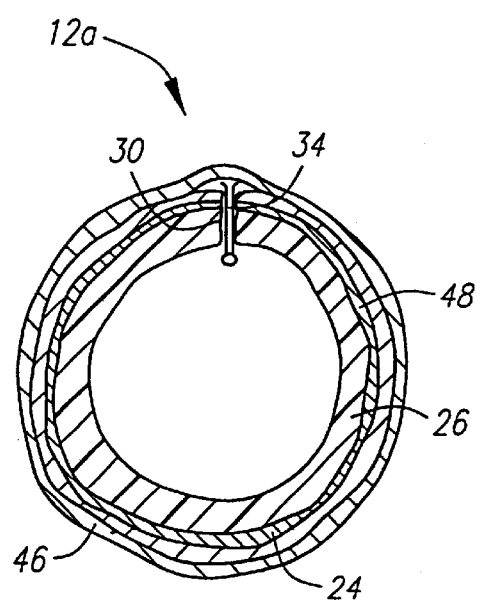
FIG. 4 is a cross-sectional view taken along lines A—A of FIG. 3.

As best seen in FIG. 4, a small opening 30 is provided through the distal end tubing 26 and cured primer coating 48 at each electrode location 24, through which an insulated ribbon cable 34 carrying a lead wire 38 and thermocouple wires 42 extends from a proximal portion of the catheter device 10 (not shown). The insulation at the ends of the lead wire 38 and thermocouple wires 42 are stripped. The lead wire 38 is electrically connected to the surface of electrode 24, e.g., by using a conductive adhesive supplemented by further application of conductive ink. A thermocouple is then formed by potting the thermocouple wires 42 to the outer surface of the distal end tubing 26 proximate the edge of the opening 30, such that the resulting thermocouple is thermally coupled, but electrically isolated, from the electrode 24.

Once the electrode construction is completed, including attachment of the respective lead and thermocouple wires 38 and 42, a protective regenerative cellulose coating 46 is applied over the entire distal end assembly 12a—i.e., over both the primer coating 48 and the electrodes 24. Several preferred processes for applying a regenerated cellulose coating or "jacket" over the distal end assembly 12a are disclosed and described in the above-incorporated U.S. Pat. No. 5,991,650.

After the regenerated cellulose coating is applied and cured, the distal end assembly 12 is again heat treated to facilitate bonding between the primer coating 48 and the regenerated cellulose coating 46, preferably to between about 100° C. and about 110° C. for about one hour.

During this later heating process, a hydrogen bond is created between the hydroxyl group of the regenerated cellulose and the hydrogen molecule of the primer coating 48. Because the primer coating 48 was originally cured prior to forming the electrodes 24, adhesion between the primer 48 and regenerated cellulose 46 is achieved only where the primer 48 is not covered by the electrodes 24.

In alternate preferred embodiments, the respective electrodes 24 may be formed over only part of the circumferential surface area of the distal end tubing 26. In this instance, the bond formed between the respective regenerated cellulose coating 46 and tubing 26 would be continuous over that part of the catheter body not covered by the electrode surface. In the alternative, the regenerated cellulose coating 46 may be selectively applied to cover only the electrode surface and not the entire circumference of the distal end tubing 26. This approach will allow the catheter device 10 to better retain its flexibility for passive or active manipulation during use, as well as reduce the "slippery" effect of the regenerated cellulose coating.

After the final curing, the distal end tubing 26, primer coating 48 and regenerated cellulose layer 46 effectively become a single composite structure, thereby preventing the regenerated cellulose 46 from substantially moving axially, radially and/or wrinkling relative to the distal end tubing 26 during use of the catheter device 10.

Figure 5:
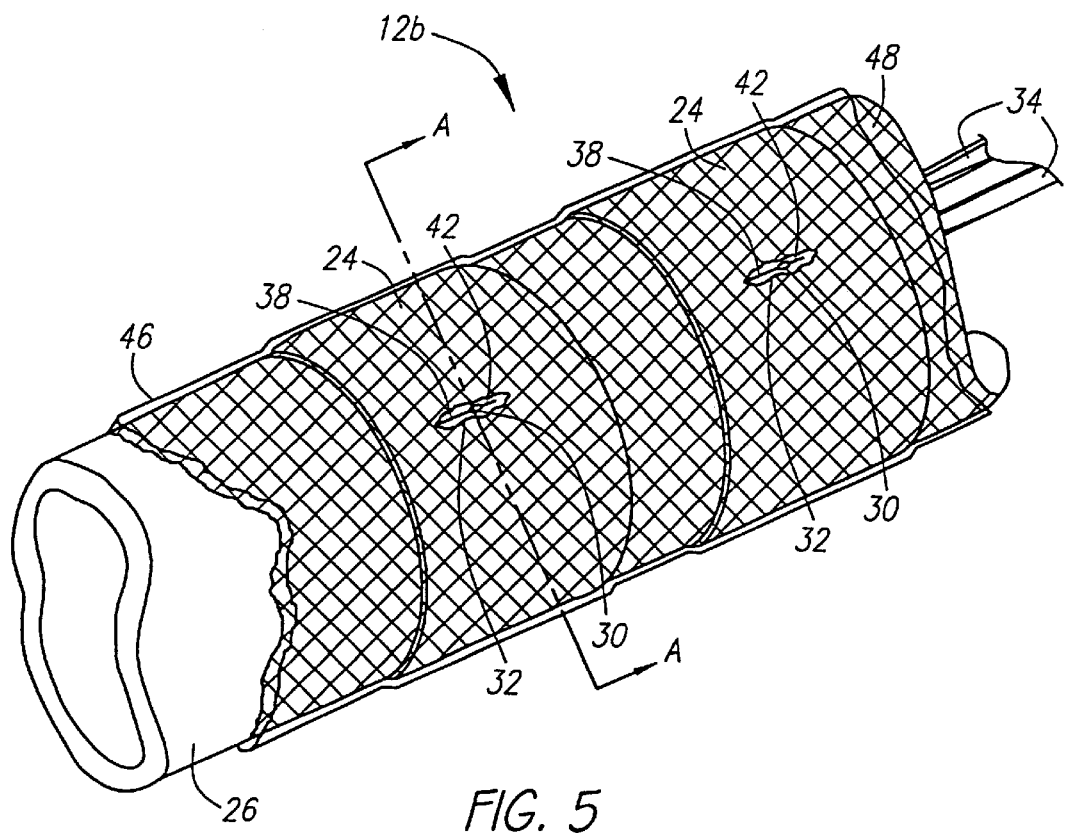
FIG. 5 is an enlarged, partially cut-away view of a second preferred distal end assembly for the catheter device of FIG. 1.
Figure 6:
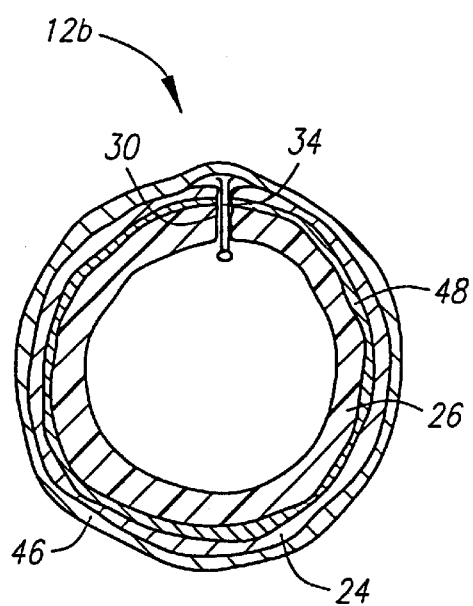
FIG. 6 is a cross-sectional view taken along lines A—A of FIG. 5.
Figure 7:
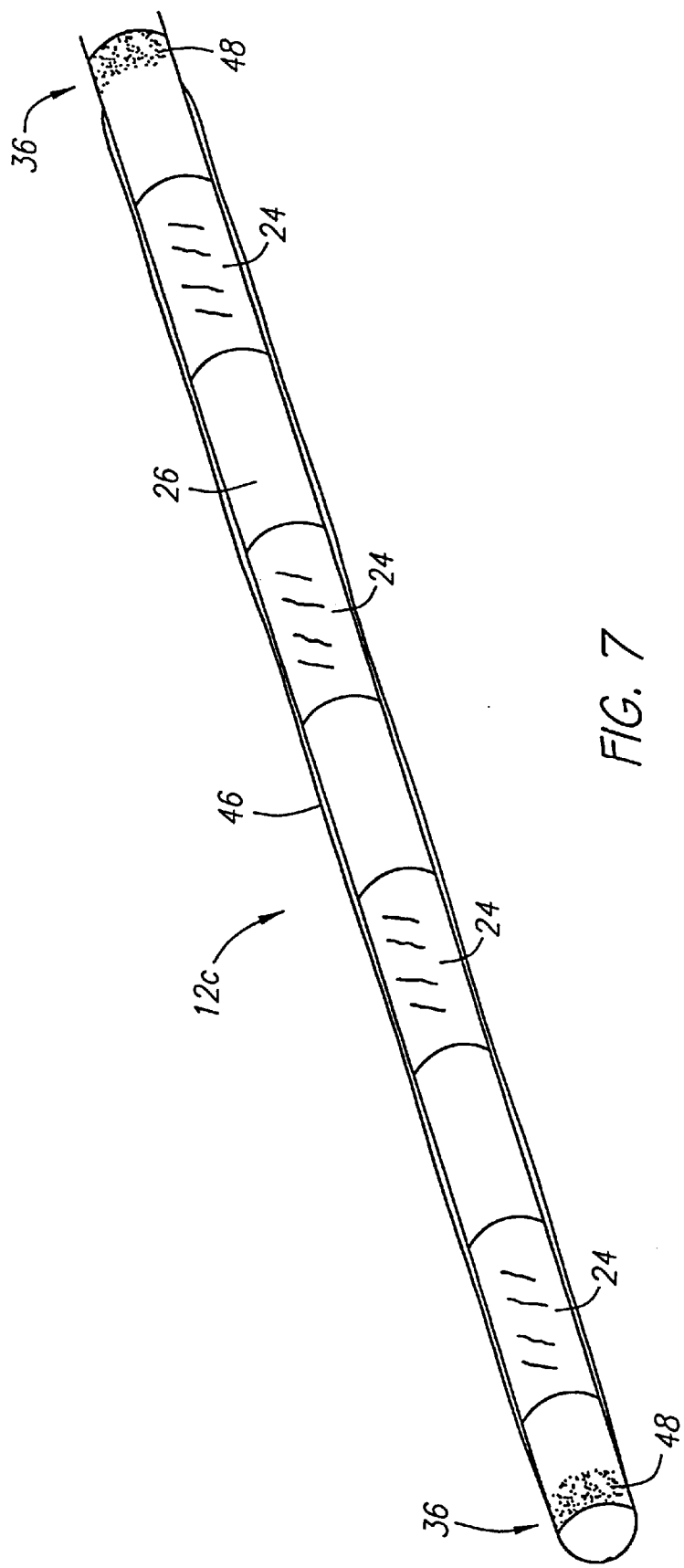
FIG. 7 is a perspective view of a distal end assembly of further alternate distal end catheter assembly.

Referring to FIGS. 5 and 6, the primer coating 48 in a second preferred distal end assembly 12b is applied after the electrodes 24 are constructed. In this instance, because the primer coating 48 substantially covers the electrodes 24, the selected primer is preferably an alternate material having a significantly lower electrical resistivity—e.g., less than about 150 ohm-cm at 500 kHz—, so as to not interfere with the electrical path between the electrodes 24 and a patient's blood stream and/or body tissue during use.

The curing process for the primer coating 48 for the distal end assembly 12b is substantially the same as discussed above in conjunction with the distal end assembly 12a. Notably, however, because many ink compounds suitable for use in electrode construction are polyurethane-based, the base coating 48 may develop a covalent bond with the ink electrodes 24, as well as with the distal end tubing 26, during the primer curing process.

In still further alternate preferred embodiments, the primer coating 48 may be applied only at predetermined locations along the length of the distal end tubing 26. By way of example, in a third preferred distal end assembly 12c illustrated in FIG. 7, the primer 48 is only applied at respective ends 36 of the distal end assembly 12c. Such an arrangement allows for ease in device construction and a wider selection of primers such as, e.g., solvent-based adhesives such as cyanoacrylate or epoxy, for the primer coating 48. In particular, employing distal end assembly 12c substantially eliminates the risk that the selected primer 48 may interfere with the conductivity of the regenerated cellulose 46 covering the electrodes 24, while still providing a sufficient bond of the outer protective layer 46 to the distal end tubing 26 for certain applications.

As will be appreciated from the present disclosure, many alternate configurations employing the underlying teachings of the present invention are possible, whereby the primer or adhesive 48 is applied only to selective areas of the catheter distal end assembly 12. By way of non-limiting example, a non-conductive primer or adhesive could be applied to the non-conductive areas of the distal end tubing 26 between the electrodes 24.

Where an adhesive such as epoxy or cyanoacrylate is used as the primer coating 48 (e.g., applied to the "bond" points 36 in the distal end assembly 12c), heat is applied to the assembly 12c after the regenerated cellulose coating 46 is formed, in order to re-activate the cyanoacrylate and bond the regenerated cellulose layer to the distal end tubing 26. Alternately, a solvent able to pass through the regenerated cellulose membrane, such as acetone or diluted nitromethane, could be used to re-activate the (previously cured) cyanoacrylate and form the bond between the regenerated cellulose coating 46 and distal end tubing 26.

In accordance with a still further alternative method, the catheter device 10, including the uncoated distal end assembly 12 including electrodes 24 and regenerated cellulose coating 46 is fully assembled without applying the primer coating 48. An adhesive such as cyanoacrylate or epoxy in a solvent carrier having a molecular size small enough to pass through the micro porous membrane of the regenerated cellulose is then applied over the regenerated cellulose coating 46 of the device, for example, at predetermined locations on the distal end assembly. The adhesive is then cured to drive off any solvents therein and bond the regenerated cellulose coating to the distal end tubing 26.

Notably, the regenerated cellulose micropore size may be controlled at the time the coating 46 is formed on the distal end assembly 12. As such, a predetermined pore size may be obtained to accommodate larger adhesive molecules, if desired. Of course, the pore size should be sufficiently small to prevent biological macromolecules, such as proteins, from passing through the regenerated cellulose structure after the bonding process is complete.

In additional alternatives, a wide variety of electrode shapes and/or sensors may be provided on a catheter device or other instrument and coated with a bonded surface coating as described herein. For example, the foregoing catheter constructions described herein may be useful in the attachment of a regenerated cellulose balloon to an anchor point on a catheter device.

Accordingly, a catheter device or other instrument made in accordance with the present invention includes a barrier that is electrically conductive, optically transparent, and/or ultrasonically transparent, yet prohibits biological macromolecules from directly or indirectly contacting the components on the instrument during use. The regenerated cellulose coating forms a closely fitting conformal sheath onto the catheter distal end assembly, that is durable and does not readily stretch substantially. Because of the protection afforded by the coating, less expensive and more efficient manufacturing procedures may be used to make the electrodes or other components on the catheter device, such as the pad printing process described above.

In addition, catheter devices are often aggressively twisted or subjected to torque during use, which may cause the coating to twist or wrinkle, potentially causing a discontinuity between the electrode and an non-bonded (i.e. mechanical interference fit) coating. Because the regenerated cellulose coating is bonded to the device, the direct contact between the coating and the underlying electrode is substantially maintained, minimizing the chance of poor, intermittent, or even lost electrical contact with the electrode. Thus, lower noise recordings, more consistent pacing thresholds, and more predictable ablation conditions may be obtained with a device manufactured in accordance with the present invention.

Thus, preferred embodiments have been disclosed of invasive medical catheters with distal end assemblies having a protective surface coating bonded thereto. While embodiments and applications of this invention have been shown and described, as would be apparent to those skilled in the art, many more modifications and applications are possible without departing from the inventive concepts herein.

The scope of the inventions, therefore, are not to be restricted except in the spirit of the appended claims.

What is claimed:

1. A catheter device, comprising:
    an elongate catheter body;
    a distal end electrode assembly integrally attached to the catheter body, wherein the distal end electrode assembly comprises at least one conductive electrode;
    a microporous coating at least partially bonded to the distal end assembly; and
    a primer coating underlying at least a portion of the microporous coating, wherein the primer coating bonds the microporous coating to the distal end assembly and wherein the primer coating covers at least a portion of one or more electrodes.

2. The catheter device of claim 1, wherein the primer coating covers all of at least one of the electrodes thereby forming at least one coated electrode.

3. The catheter device of claim 2, wherein the primer coating has an electrical resistivity such that the primer coating will not interfere with the electrical path between the coated electrodes and any biological material that the electrode assembly touches.

4. The catheter device of claim 1, wherein the primer coating covers all of each of the electrodes thereby forming one or more coated electrodes.

5. The catheter device of claim 4, wherein the primer coating has an electrical resistivity such that the primer coating will not interfere with the electrical path between the coated electrodes and any biological material that the electrode assembly touches.

6. The catheter device of claim 5, wherein the electrical resistivity is such that the primer coating will not create an electrical short between any coated electrode and any other coated electrode.

7. The catheter device of claim 1, wherein the microporous coating covers all of the electrodes.

8. The catheter device of claim 1, wherein the microporous coating covers all of the distal end electrode assembly.

9. A catheter device, comprising:
    an elongate catheter body;
    a distal end electrode assembly integrally attached to the catheter body, wherein the distal end electrode assembly comprises a plurality of conductive electrodes;
    a microporous coating at least partially bonded to the distal end assembly; and
    a primer coating underlying at least a portion of the microporous coating, wherein the primer coating bonds the microporous coating to the distal end assembly, and wherein the primer coating does not completely underlie all of the microporous coating.

10. The catheter device of claim 9, wherein the primer coating does not completely cover any of the electrodes.

11. The catheter device of claim 9, wherein the primer coating underlies less than half of the microporous coating.

12. The catheter device of claim 11, wherein the distal end electrode assembly further comprises a non-conductive polymer body that has a distal end and a proximal end and wherein the primer coating underlies the microporous coating at both the distal and proximal ends of the non-conductive polymer body.

13. The catheter device of claim 9, wherein the microporous coating covers all of the electrodes.

14. The catheter device of claim 9, wherein the microporous coating covers all of the distal end electrode assembly.

* * * * *